US012685591B2

(12) United States Patent
Junio

(10) Patent No.: US 12,685,591 B2
(45) Date of Patent: Jul. 21, 2026

(54) SYSTEMS AND METHODS FOR ROD INSERTION PLANNING AND ROD INSERTION

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 1138 days.

(21) Appl. No.: 17/575,377

(22) Filed: Jan. 13, 2022

(65) Prior Publication Data

US 2022/0241017 A1 Aug. 4, 2022

Related U.S. Application Data

(60) Provisional application No. 63/144,062, filed on Feb. 1, 2021.

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/30* (2016.02); *G16H 20/40* (2018.01); *G16H 30/40* (2018.01);
(Continued)

(58) Field of Classification Search
CPC ......... A61B 34/10; A61B 34/30; A61B 34/32; A61B 34/20; A61B 2034/107; A61B 2034/2065; A61B 2034/2048; A61B 2034/2055; A61B 2034/2059; A61B 2090/374; A61B 2090/3762; A61B 2090/378; A61B 90/37; G16H 40/63; G16H 50/50; G16H 20/40; G16H 30/40
(Continued)

(56) References Cited

U.S. PATENT DOCUMENTS 4,930,525 A * 6/1990 Palestrant .......... A61B 17/3403
6,175,758 B1 * 1/2001 Kambin ............. A61B 17/7007
(Continued)

FOREIGN PATENT DOCUMENTS

| | | |
|---|---|---|
| CN | 107157579 | 9/2017 |
| EP | 1523950 | 2/2009 |

(Continued)

OTHER PUBLICATIONS

Invitation to Pay Additional Fees for International (PCT) Patent Application No. PCT/IL2022/050131, dated May 31, 2022, 10 pages.
(Continued)

*Primary Examiner* — Ellis B. Ramirez
(74) *Attorney, Agent, or Firm* — Sheridan Ross PC

(57) ABSTRACT

Systems and methods for calculating an insertion point and a path for a rod are provided. A surgical plan having at least one image and information about a position of at least one tower may be received. The at least one image may depict a surgical region. A soft tissue portion and at least one anatomical element may be identified in the at least one image. An insertion point and a path from the insertion point to the at least one tower may be calculated based on the identified soft tissue portion and at least one anatomical element. The rod may be inserted at the insertion point and along the path.

20 Claims, 3 Drawing Sheets

200

202 — Receive a surgical plan having at least one image

204 — Identify a soft tissue portion and at least one anatomical element in the at least one image 206 — Calculate an insertion point and a path 208 — Insert a rod at the insertion point and along the path 210 — Track the rod 212 — Determine a difference between a position and/or an orientation of the rod and the path 214 — Update the path

(51) Int. Cl.
*A61B 34/30* (2016.01)
*A61B 90/00* (2016.01)
*G16H 20/40* (2018.01)
*G16H 30/40* (2018.01)

(52) U.S. Cl.
CPC . *A61B 2034/107* (2016.02); *A61B 2034/2065* (2016.02); *A61B 2090/374* (2016.02); *A61B 2090/3762* (2016.02); *A61B 2090/378* (2016.02)

(58) Field of Classification Search
USPC ............ 700/245; 701/408, 523; 706/12, 15, 706/924; 600/410, 425, 437; 606/279; 901/9
See application file for complete search history.

(56) References Cited

U.S. PATENT DOCUMENTS

| | | | | |
|---|---|---|---|---|
| 6,400,979 | B1 * | 6/2002 | Stoianovici ............ | A61B 90/36 |
| 7,237,556 | B2 | 7/2007 | Smothers et al. | |
| 8,010,181 | B2 * | 8/2011 | Smith .................... | A61B 90/11 |
| 8,394,144 | B2 | 3/2013 | Zehavi et al. | |
| 10,165,981 | B2 | 1/2019 | Schoepp | |
| 2008/0114267 | A1 * | 5/2008 | Lloyd .................... | A61B 34/20 |
| 2008/0298660 | A1 * | 12/2008 | Yamagata ............ | G01S 15/899 |
| 2009/0005679 | A1 * | 1/2009 | Dala-Krishna .......... | G06T 7/80 |
| 2014/0135617 | A1 * | 5/2014 | Schoepp ................ | A61B 5/061 |
| 2015/0150644 | A1 | 6/2015 | Lang et al. | |
| 2017/0135707 | A9 | 5/2017 | Frey et al. | |
| 2019/0029757 | A1 * | 1/2019 | Roh ........................ | G16H 20/40 |
| 2019/0231435 | A1 | 8/2019 | Zucker et al. | |
| 2019/0262084 | A1 * | 8/2019 | Roh ........................ | G16H 30/40 |
| 2020/0069438 | A1 | 3/2020 | Singh | |
| 2020/0085508 | A1 * | 3/2020 | O'Hara .................. | A61B 34/32 |
| 2020/0085509 | A1 | 3/2020 | Roh et al. | |
| 2020/0268452 | A1 | 8/2020 | Rezach et al. | |
| 2021/0137603 | A1 * | 5/2021 | Zucker .................. | A61B 17/70 |
| 2023/0008386 | A1 * | 1/2023 | Nahum .................. | G16H 30/40 |

FOREIGN PATENT DOCUMENTS

| | | | | |
|---|---|---|---|---|
| EP | 2381858 | | 11/2018 | |
| EP | 1571581 | | 7/2019 | |
| EP | 3649649 | | 5/2020 | |
| JP | H11313837 A | * | 11/1999 | ............ A61B 90/36 |
| WO | WO 2014/123130 | | 8/2014 | |
| WO | WO 2017/221257 | | 12/2017 | |

OTHER PUBLICATIONS

International Search Report and Written Opinion for International (PCT) Patent Application No. PCT/IL2022/050131, dated Jul. 21, 2022, 17 pages.

Official Action for European Patent Application No. 22709412.5, dated Mar. 2, 2026, 8 pages.

Official Action with English Translation for China Patent Application No. 202280012670.8, dated Feb. 26, 2026, 15 pages.

* cited by examiner

200

202 — Receive a surgical plan having at least one image

204 — Identify a soft tissue portion and at least one anatomical element in the at least one image 206 — Calculate an insertion point and a path 208 — Insert a rod at the insertion point and along the path 210 — Track the rod 212 — Determine a difference between a position and/or an orientation of the rod and the path 214 — Update the path

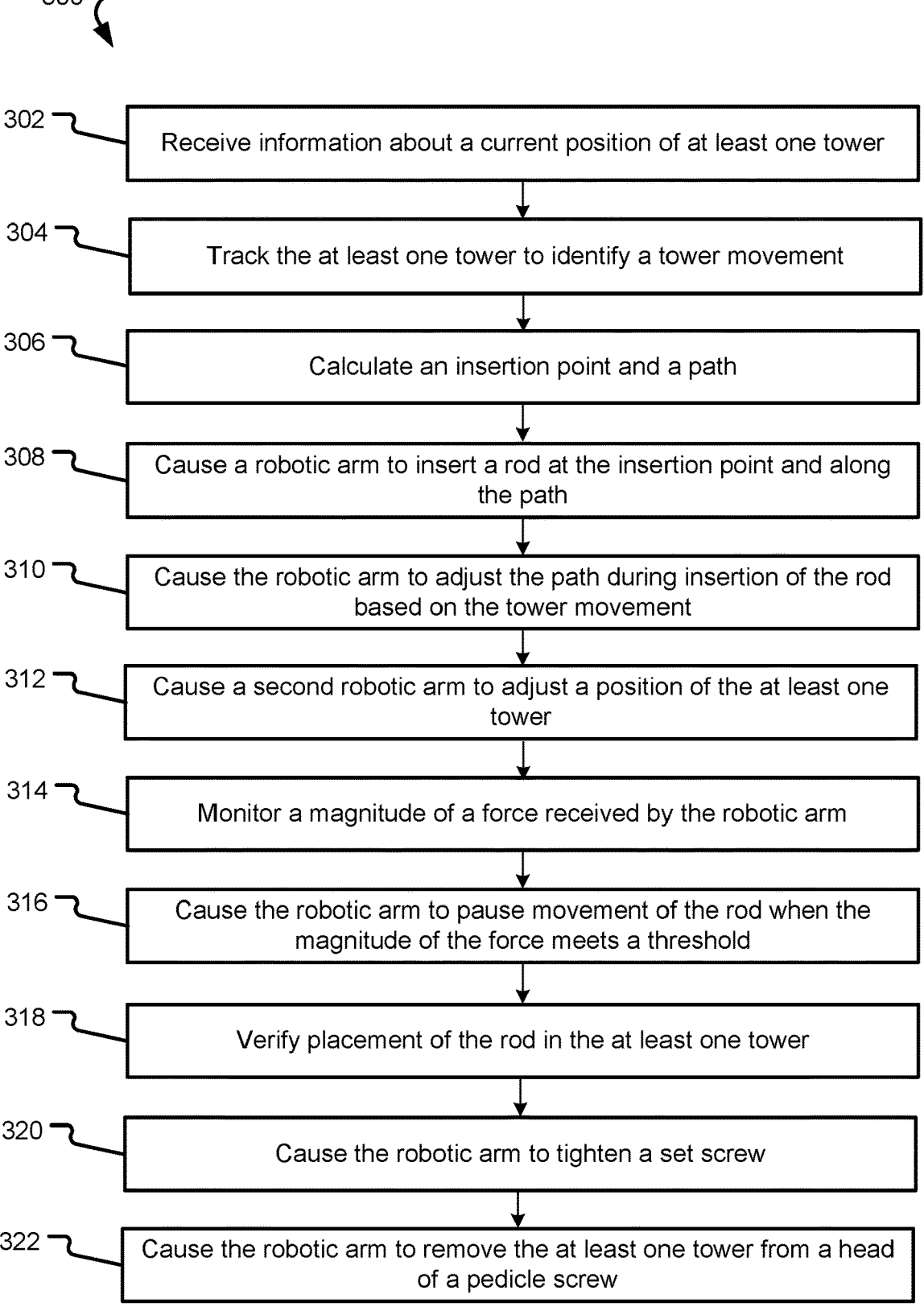

300

302 — Receive information about a current position of at least one tower

304 — Track the at least one tower to identify a tower movement

306 — Calculate an insertion point and a path

308 — Cause a robotic arm to insert a rod at the insertion point and along the path 310 — Cause the robotic arm to adjust the path during insertion of the rod based on the tower movement 312 — Cause a second robotic arm to adjust a position of the at least one tower 314 — Monitor a magnitude of a force received by the robotic arm 316 — Cause the robotic arm to pause movement of the rod when the magnitude of the force meets a threshold 318 — Verify placement of the rod in the at least one tower 320 — Cause the robotic arm to tighten a set screw 322 — Cause the robotic arm to remove the at least one tower from a head of a pedicle screw

FIG. 3

SYSTEMS AND METHODS FOR ROD INSERTION PLANNING AND ROD INSERTION

CROSS REFERENCE TO RELATED APPLICATIONS

This application claims the benefit of U.S. Provisional Application No. 63/144,062, filed on Feb. 1, 2021, and entitled "Systems and Methods for Rod Insertion Planning and Rod Insertion", which application is incorporated herein by reference in its entirety.

FIELD

The present technology relates generally to robotic surgery and relates more particularly to planning a rod insertion and executing the rod insertion using robot-assisted or robotic surgery.

BACKGROUND

Minimally invasive surgery beneficially reduces patient trauma by minimizing the size of needed incisions. Surgical robots are useful during surgeries, and may operate autonomously (e.g., without any human input during operation), semi-autonomously (e.g., with some human input during operation), or non-autonomously (e.g., only as directed by human input). In some situations, use of multiple robotic arms during a surgery can enable more to be accomplished in a shorter period of time than with only one robotic arm.

SUMMARY

Example aspects of the present disclosure include:

A robotic system for inserting a rod according to at least one embodiment of the present disclosure comprises a robotic arm comprising a proximal end; and a distal end movable relative to the proximal end, the distal end configured to position a rod; at least one processor; and a memory storing instructions for execution by the at least one processor that, when executed, cause the at least one processor to: track at least one tower to identify a tower movement, the tower extending from a head of a corresponding implanted pedicle screw; calculate an insertion point and a path from the insertion point to the at least one tower; cause the robotic arm to insert the rod at the insertion point and along the path; and cause the robotic arm to adjust the path during insertion of the rod based on the tower movement.

Any of the aspects herein, further comprising: at least one sensor, wherein the memory stores additional instructions for execution by the at least one processor that, when executed, further cause the at least one processor to: monitor a magnitude of a force received by the robotic arm using the at least one sensor.

Any of the aspects herein, wherein the memory stores additional instructions for execution by the at least one processor that, when executed, further cause the at least one processor to: cause the robotic arm to pause movement of the rod when the magnitude of the force meets a threshold.

Any of the aspects herein, wherein the memory stores additional instructions for execution by the at least one processor that, when executed, further cause the at least one processor to: cause the robotic arm to tighten a set screw of the corresponding pedicle screw.

Any of the aspects herein, wherein the memory stores additional instructions for execution by the at least one processor that, when executed, further cause the at least one processor to: cause the robotic arm to remove the at least one tower from the head of the corresponding pedicle screw.

Any of the aspects herein, wherein tracking the at least one tower uses at least one of a navigation system, a marker, or a sensor.

Any of the aspects herein, wherein causing the robotic arm to adjust the path includes adjusting at least one of an orientation of the rod or a position of the rod.

Any of the aspects herein, wherein the memory stores additional instructions for execution by the at least one processor that, when executed, further cause the at least one processor to: verify placement of the rod in the at least one tower.

Any of the aspects herein, wherein verifying placement of the rod in the at least one tower uses at least one of a laser pointer and reflector, a navigation system, a sensor, or a marker.

A robotic system for inserting a rod according to at least one embodiment of the present disclosure comprises a first robotic arm and a second robotic arm, each robotic arm comprising: a proximal end; and a distal end movable relative to the proximal end, wherein the distal end of the first robotic arm is configured to position a rod and the distal end of the second robotic arm is configured to hold at least one tower in a known position, the at least one tower extending from a head of a corresponding pedicle screw implanted in a vertebra of a plurality of vertebrae; at least one processor; and a memory storing instructions for execution by the at least one processor that, when executed, cause the at least one processor to: receive position information about a current position of the at least one tower; calculate an insertion point and a path from the insertion point to the at least one tower based on the current position; and cause the first robotic arm to insert the rod at the insertion point and along the calculated path.

Any of the aspects herein, wherein the position information is received from at least one sensor of the second robotic arm.

Any of the aspects herein, further comprising: a tracking marker positioned on the second robotic arm; and a navigation system configured to generate the position information based on detected movement of the tracking marker.

Any of the aspects herein, further comprising at least one sensor, and wherein the memory stores additional instructions for execution by the at least one processor that, when executed, further cause the at least one processor to: verify, by the at least one sensor, placement of the rod in the at least one tower.

Any of the aspects herein, wherein the memory stores additional instructions for execution by the at least one processor that, when executed, further cause the at least one processor to: cause the first robotic arm to tighten a set screw of the corresponding pedicle screw.

Any of the aspects herein, wherein the memory stores additional instructions for execution by the at least one processor that, when executed, further cause the at least one processor to: cause the first robotic arm to remove the tower from the head of the corresponding pedicle screw.

Any of the aspects herein, wherein the current position is different than the known position, and the memory stores additional instructions for execution by the at least one processor that, when executed, further cause the at least one processor to: cause the first robotic arm to adjust the path during insertion of the rod when a difference between the current position and the known position meets a predetermined threshold.

Any of the aspects herein, wherein the current position is different than the known position, and the memory stores additional instructions for execution by the at least one processor that, when executed, further cause the at least one processor to: cause the second robotic arm to adjust a position of the at least one tower based on a difference between the current position and the known position meeting a predetermined threshold.

A method for inserting a rod according to at least one embodiment of the present disclosure comprises tracking at least one tower extending from a corresponding implanted pedicle screw to detect movement of the at least one tower; calculating an insertion point and a path from the insertion point to the at least one tower; causing a robotic arm to insert the rod at the insertion point and along the path; and causing the robotic arm to adjust the path during insertion of the rod based on the detected movement.

Any of the aspects herein, further comprising: causing the robotic arm to remove the tower from the corresponding pedicle screw.

Any of the aspects herein, further comprising: causing the robotic arm to tighten a set screw of the corresponding pedicle screw.

Any of the aspects herein, wherein tracking the at least one tower uses at least one of a navigation system, a marker, or a sensor.

Any of the aspects herein, further comprising: verifying placement of the rod in the at least one tower.

A robotic system for inserting a rod according to at least one embodiment of the present disclosure comprises a robotic arm comprising: a proximal end; and a distal end movable relative to the proximal end, the distal end configured to hold at least one tower in a known position; at least one processor; and a memory storing instructions for execution by the at least one processor that, when executed, cause the at least one processor to: calculate an insertion point and a path from the insertion point to the at least one tower; generate instructions for inserting a rod along the path; and update the path during insertion of the rod based on information about a position of the rod or movement of the tower.

Any of the aspects herein, further comprising: at least one sensor, wherein the memory stores additional instructions for execution by the at least one processor that, when executed, further cause the at least one processor to: monitor a magnitude of a force received by the robotic arm using the at least one sensor.

Any of the aspects herein, wherein the memory stores additional instructions for execution by the at least one processor that, when executed, further cause the at least one processor to: cause the robotic arm to release the tower when the magnitude of the force meets a threshold.

Any of the aspects herein, wherein the memory stores additional instructions for execution by the at least one processor that, when executed, further cause the at least one processor to: cause the robotic arm to tighten a set screw of a pedicle screw corresponding to the tower.

Any of the aspects herein, wherein the memory stores additional instructions for execution by the at least one processor that, when executed, further cause the at least one processor to: cause the robotic arm to remove the at least one tower from a head of a pedicle screw corresponding to the tower.

Any of the aspects herein, wherein the memory stores additional instructions for execution by the at least one processor that, when executed, further cause the at least one processor to: cause the robotic arm to move the tower from the known position to an updated position based at least one of a force exerted on the robotic arm or information about a position of the rod.

Any of the aspects herein, wherein the memory stores additional instructions for execution by the at least one processor that, when executed, further cause the at least one processor to: verify placement of the rod in the at least one tower.

Any of the aspects herein, wherein verifying placement of the rod in the at least one tower uses at least one of a laser pointer and reflector, a navigation system, a sensor, or a marker.

A method for calculating an insertion point and a path for a rod according to at least one embodiment of the present disclosure comprises receiving a surgical plan having at least one image and information about a position of at least one tower, the at least one image depicting a surgical region; identifying, in the at least one image, a soft tissue portion and at least one anatomical element; calculating an insertion point and a path from the insertion point to the at least one tower based on the identified soft tissue portion and at least one anatomical element; and causing a robotic arm to insert a rod at the insertion point and along the path.

Any of the aspects herein, wherein the at least one image is obtained from at least one of an MRI scanner, an ultrasound, or a CT scanner.

Any of the aspects herein, wherein the at least one image comprises a first image and a second image of the surgical region, the first image comprising hard tissue information and the second image comprising soft tissue information.

Any of the aspects herein, wherein the first image is generated using a first imaging modality and the second image is generated using a second imaging modality.

Any of the aspects herein, wherein the first image is a CT image and the second image is an ultrasound image.

Any of the aspects herein, wherein one of the first and second images is a preoperative image, and another of the first and second images is an intraoperative image.

Any of the aspects herein, wherein calculating the insertion point and the path is based on one or more inputs.

Any of the aspects herein, wherein identifying the at least one anatomical element uses at least one of feature recognition, machine learning, artificial intelligence, or a neural network.

Any of the aspects herein, wherein identifying the soft tissue portion uses segmentation.

Any of the aspects herein, wherein calculating the insertion point and the path is based on information about a geometry of the rod.

Any of the aspects herein, further comprising: updating the path based on detected movement of the soft tissue portion during insertion of the rod along the path.

Any of the aspects herein, further comprising: updating the path based on detected movement of the at least one tower.

A method for inserting a rod according to at least one embodiment of the present disclosure comprises receiving a surgical plan having information about an insertion point and a path of a rod to at least one tower; causing a robotic arm to insert the rod at the insertion point using the path; tracking the rod during insertion of the rod using the path; determining a difference between a pose of the rod and the path; and updating the path when the difference meets a threshold.

Any of the aspects herein, wherein the updated path is communicated to a user.

Any of the aspects herein, wherein tracking the rod includes tracking a soft tissue portion surrounding the rod.

Any of the aspects herein, wherein the surgical plan includes at least one image depicting a surgical region, and further comprising: identifying, in the at least one image, a soft tissue portion and at least one anatomical element; and calculating the insertion point and path from the insertion point to the at least one tower based on the identified soft tissue portion and at least one anatomical element.

Any of the aspects herein, wherein the at least one image is obtained from an MRI scanner.

Any of the aspects herein, wherein calculating the insertion point and the path is based on one or more inputs.

Any of the aspects herein, wherein identifying the at least one anatomical element uses at least one of feature recognition, machine learning, artificial intelligence, or a neural network.

Any of the aspects herein, wherein identifying the soft tissue portion uses segmentation.

Any of the aspects herein, wherein calculating the insertion point and the path is based on information about a geometry of the rod.

Any of the aspects herein, wherein tracking the rod uses at least one of a navigation system, a marker, or a sensor.

A system for calculating an insertion point and a path for a rod according to at least one embodiment of the present disclosure comprises at least one processor; and at least one memory storing instructions for execution by the at least one processor that, when executed, cause the at least one processor to: receive a surgical plan having at least one image and information about a position of at least one tower, the at least one image depicting a surgical region; identify a soft tissue portion and at least one anatomical element; calculate an insertion point and path from the insertion point to the at least one tower based on the identified soft tissue portion and at least one anatomical element, the at least one tower extending from an implanted pedicle screw; and cause a robotic arm to insert a rod at the insertion point and along the path.

Any of the aspects herein, wherein the at least one image is obtained from at least one of an MRI scanner, an ultrasound, or a CT scanner.

Any of the aspects herein, wherein the at least one image comprises a first image and a second image of the surgical region, the first image comprising hard tissue information and the second image comprising soft tissue information.

Any of the aspects herein, wherein the first image is generated using a first imaging modality and the second image is generated using a second imaging modality.

Any of the aspects herein, wherein the first image is a CT image and the second image is an ultrasound image.

Any of the aspects herein, wherein one of the first and second images is a preoperative image, and another of the first and second images is an intraoperative image.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_0$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 3 is another flowchart of a method according to at least one embodiment of the present disclosure.

DETAILED DESCRIPTION

Figure 1:
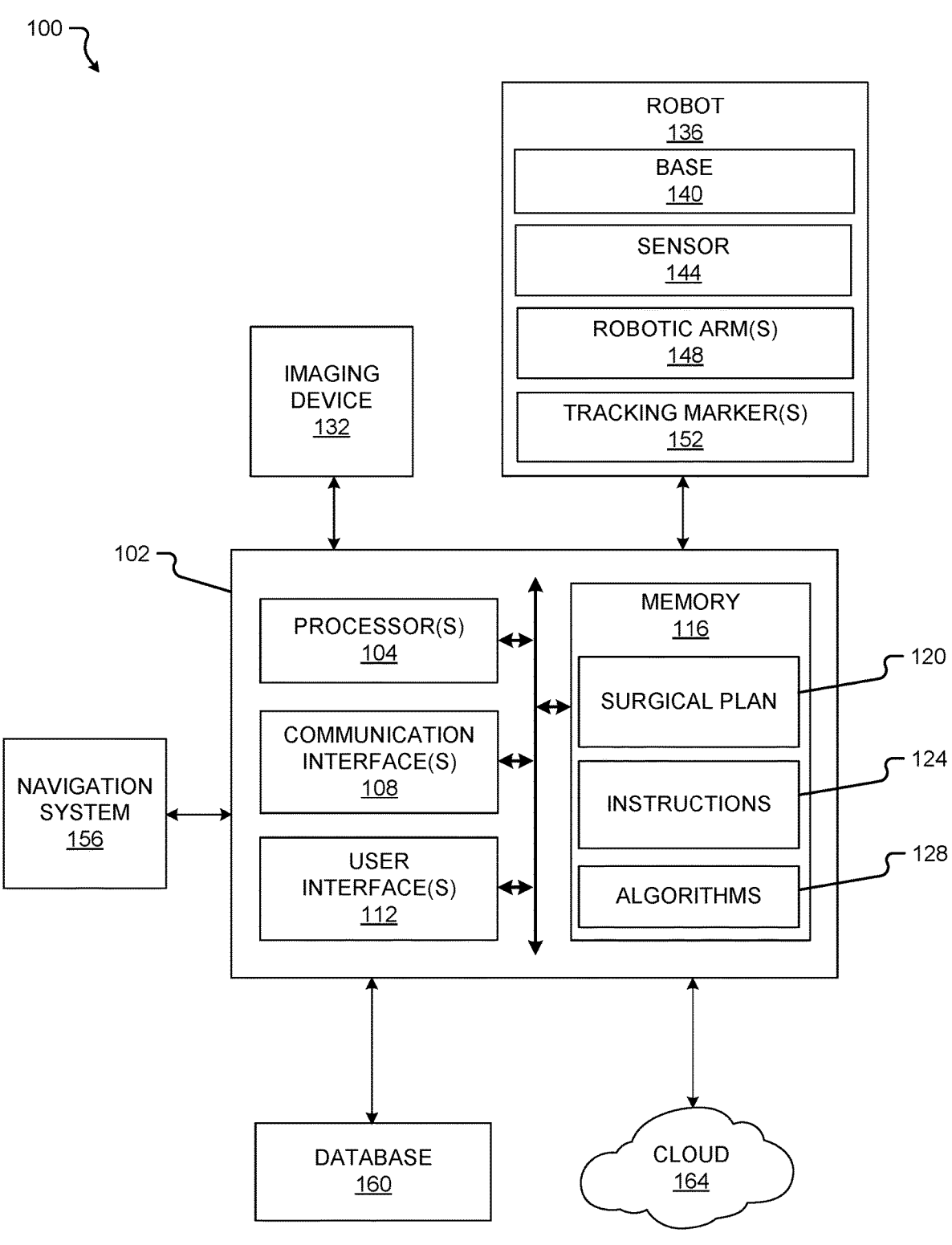
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Minimally invasive surgery (MIS) techniques are increasing in use for spinal procedures. Surgeons performing MIS may encounter hurdles in rod fusion cases when inserting the rod into a patient's back. The procedure includes using towers attached to inserted pedicle screws that act as screw extenders and allow for a rod (inserted from a small incision) to be slid into each tower in succession. After the rod is inside all of the towers, the rod is locked into place using set screws in each tower. The procedure is time consuming and not robust in its duration. Complexity of the procedure also increases with an increase in more screws needed. Typical spine surgeons try to avoid performing the procedure on more than 3-4 spine levels.

According to embodiments of the present disclosure, a surgeon may plan a surgical procedure on a robotic platform (or using any computer with a user interface, and providing the plan to a robotic platform). A preoperative image may be used to plan the surgical procedure. The preoperative image may be obtained from an MRI or other imaging device. Anatomical element(s) may be identified in the preoperative image using, for example, a machine-learning based tissue algorithm (e.g., U-net). Soft tissue may be identified using tissue segmentation to identify main blood vessels, nerves, nerve roots, muscle tissue, bone, ligaments, and/or large organs. Preoperative planning may also include identifying desired implants (including rods) and determining a desired position of the implants. The implants may then be inserted. An insertion point and a path for a rod to at least one tower may be calculated based on the identified soft tissue and anatomical element(s) in the at least one image and/or the location of the inserted implants. The rod may be inserted at the insertion point and along the path to place the rod in the at least one tower. The at least one tower may be tracked to identify tower movement during insertion of the rod. The path may be updated when tower movement is identified or movement of the rod offset from the path is identified. Embodiments of the present disclosure also provide for using a robotic arm to insert the rod at the insertion point and to move the rod along the path. In some embodiments, a first robotic arm may insert the rod and a second robotic arm may support the at least one tower.

Some embodiments of the present disclosure provide for calculating a path for rod insertion, for either robotic or non-robotic insertion without rod tracking. A patient may undergo a pre-operative MRI and a software may perform a machine-based tissue recognition using an algorithm (such as U-net, for example) on anatomical features of the patient's designated spine section shown in the MRI. Tissue segmentation is then executed to segment main blood vessels, nerves and nerve roots, muscle tissue, bone, ligaments, and other large organs. Pre-operative and/or intra-operative planning is done on the MRI, including determining the desired implants and rods. The procedure is then executed to implant the desired implants. The location for the rod insertion is calculated including optimizing an insertion point (based on a geometry of the rod and the tissue). The path is calculated using different inputs such as avoiding main blood vessels, avoiding identified nerves and nerve roots, aligning the rod to run as parallel as possible to muscle structures, minimize the amount of ligaments transfers, minimize needed rod rotations in a path of motion, avoid rod insertion into non-relevant organs, avoid rod collision with bony anatomy, and/or data presented to the surgeon.

Some embodiments of the present disclosure provide for calculating a path for rod insertion, for either robotic or non-robotic insertion with rod tracking. A patient may undergo a pre-operative MRI and a software may perform a machine-based tissue recognition using an algorithm (such as U-net, for example) on anatomical features of the patient's designated spine section shown in the MRI. Tissue segmentation is then executed to segment main blood vessels, nerves and nerve roots, muscle tissue, bone, ligaments, and other large organs. Pre-operative and/or intra-operative planning is done on the MRI, including determining the desired implants and rods. The procedure is then executed to implant the desired implants. The location for the rod insertion is calculated including optimizing an insertion point (based on a geometry of the rod and the tissue). The path is calculated using different inputs such as avoiding main blood vessels, avoiding identified nerves and nerve roots, aligning the rod to run as parallel as possible to muscle structures, minimize the amount of ligaments transfers, minimize needed rod rotations in a path of motion, avoid rod insertion into non-relevant organs, avoid rod collision with bony anatomy, and/or data presented to the surgeon. Further, the rod may be tracked using, for example, inertial measuring units, navigation at the rod's distal end, and/or electromagnetic sensors. A software may also display a needed rod direction and orientation to a user. The software may also update a rod path and orientation as the rod moves.

Embodiments of the present disclosure also provide for tracking towers during rod insertion using one robotic arm. A single arm may insert the rod while the towers location may be tracked. Surgery may be planned and executed up to a point where the towers are located or implanted in the patient's anatomy (with or without a robot). Each of the relevant towers may be tracked using navigation, reflectors, inertial measurement units, or other methods. A rod shape is known or measured (e.g., could be measured by a navigation probe that runs on the rod) and the rod can be attached in a known position and orientation to a robot. A path for an insertion point and path to the towers may be calculated. The robot may execute the rod insertion according to the calculated path. As the towers are in a tracked location, the robot path may adjust as the towers move (the towers may move as the towers are flexible and the rod is moving and shifting from within the patient's body).

Embodiments of the present disclosure also provide for tracking towers during rod insertion using multiple robots acting as the rod inserters. Surgery may be planned and executed up to a point where the towers are located or implanted in the patient's anatomy (with or without a robot). While the procedure takes place, one of the robotic arms may hold the tower(s) in a known, constantly measured location (the robot may have a tower holding end effector and safety mechanisms to avoid harm). A rod shape is known or measured (e.g., which may be measured by a navigation probe that runs on the rod) and the rod can be attached in a known position and orientation to a robot. A path for an insertion point and path to the towers may be calculated. The robot may execute the rod insertion according to the calculated path. As the towers are held by the first robotic arm(s) in a tracked location, and as the robot knows the location of the first robotic arm(s), the robotic arm inserting the rod may adjust the path of the rod as the towers move (the towers may move as the towers are flexible and the rod is moving and shifting from within the patient's body). Alternatively, the path of the rod inserting robot may not change while the robot holding the towers moves the towers (within their calculated limits) to align with the rod path. In other embodiments, the robotic arm inserting the rod may adjust the path as the towers move and the robotic arm(s) holding the towers may move the towers. The robotic arm(s) holding the towers can then communicate if the rod is inside the designated tower which can be done by (i) an electrical circuit closing (e.g., between two robots), (ii) a laser pointer and reflector, (iii) visual lights with algorithms or rod marking identification. The path can be updated if changes occur to the needed path. The rotation orientation of the rod may change according to the needed fixation (i.e., many surgeons insert the rod in one orientation for ease of insertion and then rotate it to the right orientation). The rod holding robot may tighten in the set screws that hold the rod in place. The rod holding robot may also break up the tower extenders.

Embodiments of the present disclosure provide technical solutions to the problems of (1) improving the success of rod insertion in a spinal procedure, and in particular in an MIS spinal procedure; (2) improving rod insertion planning; (3) reducing a duration of the spinal procedure by accounting and adjusting for movement in pedicle screw towers; (4) increasing the number of levels that may be successfully reached in an MIS spine surgery; and/or (5) increasing patient safety during robot-assisted or robotic minimally invasive surgeries.

Turning first to FIG. 1, a block diagram of a system 100 according to at least one embodiment of the present disclosure is shown. The system 100 may be used, for example: to calculate an insertion point and a path for a rod to a tower; to adjust the path when movement of the tower or movement of the rod offset from the path is identified; to carry out one or more aspects of one or more of the methods disclosed herein; for navigation purposes; to carry out a fully autonomous and/or a robot-assisted surgery using a plurality of robots; or for any other useful purpose.

The system 100 comprises a computing device 102, an imaging device 132, a robot 136, a navigation system 156, a database 160, and a cloud 164. Notwithstanding the foregoing, systems according to other embodiments of the present disclosure may omit any one or more of the computing device 102, the imaging device 132, the robot 136, the navigation system 156, the database 160, and/or the cloud 164. Additionally, systems according to other embodiments of the present disclosure may arrange one or more components of the system 100 differently (e.g., one or more of the imaging device 132, the robot 136, and/or the navigation system 156 may comprise one or more of the components shown in FIG. 1 as being part of the computing device 102). Still further, systems according to other embodiments of the present disclosure may comprise two or more of any of the components described herein, including, for example, the imaging device 132, the robot 136, and/or the database 160.

The computing device 102 comprises at least one processor 104, at least one communication interface 108, at least one user interface 112, and at least one memory 116. A computing device according to other embodiments of the present disclosure may omit one or both of the communication interface(s) 108 and the user interface(s) 112.

The at least one processor 104 of the computing device 102 may be any processor identified or described herein or any similar processor. The at least one processor 104 may be configured to execute instructions 124 stored in the at least one memory 116, which instructions 124 may cause the at least one processor 104 to carry out one or more computing steps utilizing or based on data received, for example, from the imaging device 132, the robot 136, the navigation system 156, the database 160, and/or the cloud 164.

The computing device 102 may also comprise at least one communication interface 108. The at least one communication interface 108 may be used for receiving image data or other information from an external source (such as an imaging device 132, a robot 136, the navigation system 156, the database 160, the cloud 164, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the imaging device 132, the robot 136, the navigation system 156, the database 160, the cloud 164, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the computing device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, headset, eyewear, or wearable device, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102, the imaging device 132, the robot 136, and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the methods 200 or 300 described herein. The at least one memory 116 may store, for example, instructions 124 for execution by the at least one processor 104, for example to cause the at least one processor 104 to carry out one or more of the steps of the methods 200 and/or 300; and/or one or more algorithms 128 for use by the processor in carrying out any calculations necessary to complete one or more of the steps of the methods 200 and/or 300 (e.g., to calculate an insertion point and path, and so forth), or for any other calculations. Such instructions 124 and/or algorithms 128 may, in some embodiments, be organized into one or more applications, modules, packages, layers, or engines, and may cause the at least one processor 104 to manipulate data stored in the at least one memory 116 and/or received from or via another component of the system 100. The at least one memory 116 may also store one or more surgical plans 120

The imaging device 132 may be operable to image anatomical feature(s) (e.g., a bone, veins, tissue, etc.) and/or other aspects of patient anatomy, and/or any surgical instruments or tools within the field of view of the imaging device 132, to yield image data (e.g., image data depicting or corresponding to a bone, veins, tissue, implants, tools, etc.). The imaging device 132 may be capable of taking a 2D image or a 3D image to yield the image data. "Image data" as used herein refers to the data generated or captured by an imaging device 132, including in a machine-readable form, a graphical/visual form, and in any other form. In various examples, the image data may comprise data corresponding to an anatomical feature of a patient, or to a portion thereof. The imaging device 132 may be or comprise, for example, an ultrasound scanner (which may comprise, for example, a physically separate transducer and receiver, or a single ultrasound transceiver), a radar system (which may comprise, for example, a transmitter, a receiver, a processor, and one or more antennae), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography scanner, an endoscope, a microscope, a thermographic camera (e.g., an infrared camera), or any other imaging device 132 suitable for obtaining images of an anatomical feature of a patient.

In some embodiments, the imaging device 132 may comprise more than one imaging device 132. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 132 may be operable to generate a stream of image data. For example, the imaging device 132 may be configured to operate with an open shutter, or with a shutter that continuously alternates between open and shut so as to capture successive images.

The robot 136 may be any surgical robot or surgical robotic system. The robot 136 may be or comprise, for example, the Mazor X™ Stealth Edition robotic guidance system. The robot 136 may comprise a base 140 that supports a robotic arm 148. The robot 136 may comprise one or more robotic arms 148 (e.g., some robots 136 may comprise two robotic arms 148, three robotic arms 148, four robotic arms 148, or another number of robotic arms 148). Each robotic arm 148 may, in some embodiments, assist with a surgical procedure (e.g., by holding and inserting a rod at an insertion point and along a path, by holding at least one tower) and/or automatically carry out a surgical procedure.

Each robotic arm 148 may have three, four, five, six, or more degrees of freedom.

The robot 136 also comprises one or more sensors 144. The sensor 144 may be a force sensor, configured to detect a force applied on the robotic arm 148 (e.g., whether via an end effector of the robotic arm 148, a tool held by an end effector of the robotic arm 148, or otherwise). The sensor 144 may be an inertial measurement unit sensor, position sensor, a proximity sensor, a magnetometer, or an accelerometer. In some embodiments, the sensor 144 may be a linear encoder, a rotary encoder, or an incremental encoder. In still other embodiments, the sensor 144 may be an imaging sensor. Other types of sensors may also be used as the sensor 144. The one or more sensors 144 may be positioned, for example, on the robotic arm 148 or elsewhere.

Data from the sensor(s) 144 may be provided to a processor of the robot 136, to the processor 104 of the computing device 102, and/or to the navigation system 156. The data may be used to calculate a pose of the robotic arm 148, of an end effector of the robotic arm 148, and/or of a tool or other device attached to the robotic arm 148 (whether via an end effector or otherwise). The calculation may be based not just on data received from the sensor(s) 144, but also on data or information (such as, for example, physical dimensions) about, for example, the robot 136 or a portion thereof, or any other relevant object, which data or information may be stored, for example, in a memory 116 of a computing device 102 or in any other memory. The data may also be used to detect if a force received by the robotic arm 148 (which may be a force received by a tool supported by the robotic arm 148) exceeds a predetermined threshold.

One or more tracking markers 152 may be fixedly secured to or positioned on the robot 136, whether on the base 140, the robotic arm 148, and/or elsewhere. In some embodiments, one or more tracking markers 152 may additionally or alternatively be affixed to one or more other components of the system 100. The tracking markers 152 may be useful for enabling the navigation system 156 to determine and/or track a position of the robot 136 (or any other component to which one or more tracking markers 152 are secured). In some embodiments, one or more tracking markers 152 (or similar tracking markers) may be affixed to a patient undergoing a surgical procedure, so as to enable an imaging device 132, a navigation system 156, or another system or device to track a position of the patient.

The navigation system 156 of the system 100 may provide navigation for a surgeon and/or for the robot 136 during an operation. The navigation system 156 may be any now-known or future-developed navigation system, including, for example, the Medtronic StealthStation™ S8 surgical navigation system. The navigation system 156 may include a camera or other sensor(s) for detecting and/or tracking one or more reference markers, navigated tracking markers, or other objects within an operating room or other room where a surgical procedure takes place. In various embodiments, the navigation system 156 may be used to track a position of the robotic arm 148 (or, more particularly, of one or more tracking markers 152 attached to the robotic arm 148) of each robot 136. The navigation system 156 may be used to track a position of one or more reference frames, markers, or arrays or other structures useful for detection by a camera or other sensor of the navigation system 156. The navigation system 156 may be used, for example, to detect a position of a reference frame mounted to a patient and/or a position of one or more robotic arms 148. The navigation system 156 may include a display for displaying one or more images from an external source (e.g., the computing device 102, the imaging device 132, a database 160, the cloud 164, or another source) or a video stream from the camera or other sensor of the navigation system 156. In some embodiments, the system 100 may operate without the use of the navigation system 156.

The database 160 may store information that correlates one coordinate system to another (e.g., one or more robotic coordinate systems to a patient coordinate system and/or to a navigation coordinate system). The database 160 may additionally or alternatively store, for example, information about or corresponding to one or more characteristics of the tracking markers 152; one or more surgical plans 120 (including, for example, image information about a patient's anatomy at and/or proximate the surgical site, for use by the robot 136, the navigation system 156, and/or a user of the computing device 102 or of the system 100); one or more images useful in connection with a surgery to be completed by or with the assistance of one or more other components of the system 100; and/or any other useful information. The database 160 may be configured to provide any such information to the computing device 102 or to any other device of the system 100 or external to the system 100, whether directly or via the cloud 164. In some embodiments, the database 160 may be or comprise part of a hospital image storage system, such as a picture archiving and communication system (PACS), a health information system (HIS), and/or another system for collecting, storing, managing, and/or transmitting electronic medical records including image data.

The cloud 164 may be or represent the Internet or any other wide area network. The computing device 102 may be connected to the cloud 164 via the communication interface 108, using a wired connection, a wireless connection, or both. In some embodiments, the computing device 102 may communicate with the database 160 and/or an external device (e.g., a computing device) via the cloud 164.

Figure 2:
FIG. 2 is a flowchart of a method according to at least one embodiment of the present disclosure.
Figure 2:
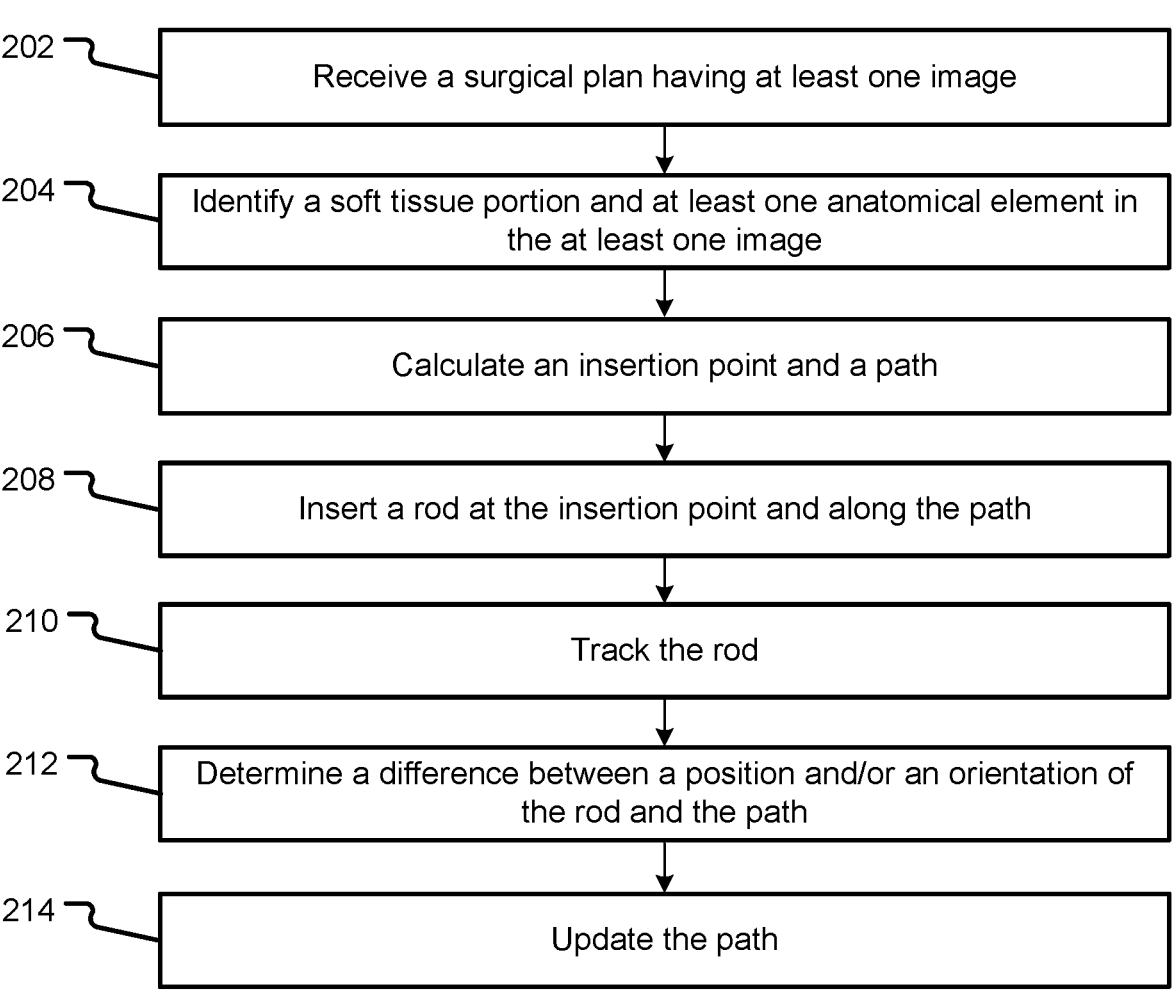

FIG. 2 depicts a method 200 for a planning a rod insertion and more specifically, for calculating an insertion point and a path for a rod. The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 136) or part of a navigation system (such as a navigation system 156). A processor other than any processor described herein may also be used to execute the method 200. The at least one processor may perform the method 200 by executing instructions stored in a memory, such as the instructions 124 of the memory 116. The instructions may correspond to one or more steps of the method 200 described below. The instructions may cause the processor to execute one or more algorithms, such as the algorithms 128. For example, one or more such algorithms 128 may be used to identify soft tissue and at least one anatomical element in at least one image, calculate an insertion point and a path from the insertion point to at least one tower, and/or determine a difference between a position and/or an orientation of a rod and the path.

The method 200 comprises receiving a surgical plan (step 202). The surgical plan may be the same as or similar to the surgical plan 120. The surgical plan may be received via a user interface (e.g., the user interface 112) and/or a communication interface (e.g., the communication interface 108) of a computing device such as the computing device 102, and may be stored in a memory such as the memory 116 of the computing device. The surgical plan may include information about at least one tower of at least one pedicle screw. The information may include information about placement of and/or a position and/or orientation of the at least one pedicle screw. The information may also include at least one dimension of the at least one tower. The surgical plan may also include information about at least one anatomical element. For example, the information may identify a vertebra that the pedicle screw may be implanted into.

The surgical plan may also include at least one image depicting a surgical region. The at least one image may be obtained from an imaging device such as the imaging device 132. In some embodiments, the at least one image is obtained from or otherwise corresponds to an MRI. In other embodiments, the at least one image comprises an ultrasound image, a CT image, or an image generating using an imaging modality other than magnetic resonance and/or ultrasound. The image may be obtained prior to a surgical procedure (e.g., preoperatively) or during the surgical procedure (e.g., intraoperatively). For example, the at least one image may be obtained after the at least one pedicle screw is implanted.

In some embodiments, the at least one image may comprise a first image and a second image of a surgical region. In some instances, the first image or the second image may be a preoperative image or an intraoperative image. The first image may comprise hard tissue information and the second image may comprise soft tissue information. The first image may be generated, for example, using a first imaging modality such as a CT scanner. The second image may be generated, for example, using a second imaging modality such as an ultrasound image. In some embodiments, the first image and the second image may be combined. For example, the soft tissue information of the second image may be combined with or added to the hard tissue information of the first image.

The method 200 also comprises identifying at least a soft tissue portion and at least one anatomical element in the at least one image (step 204). In some embodiments, the identifying can be performed automatically by an algorithm such as the algorithm 128. In other embodiments, the identifying can be performed by a surgeon or other user. Identifying the soft tissue portion and/or at least one anatomical element may include annotating or otherwise labeling each anatomical element and/or soft tissue element in the image. In some embodiments, identifying the soft tissue portion comprises segmenting the at least one image using one or more image processing algorithms. The anatomical elements may be or include one or more of, for example, bones, organs, arteries, muscles, ligaments, nerves, and/or any other anatomical elements. The soft tissue portion may be or include, for example, blood vessels, nerves, nerve roots, muscle tissue, ligaments, and/or organs. The at least one anatomical element and the soft tissue portion may or may not be mutually exclusive (e.g., an organ in the image may be identified as soft tissue portion and as an anatomical element).

In some embodiments, identifying the at least one anatomical element uses feature recognition (using, e.g., an edge detection or other feature recognition algorithm). For example, a contour of a vertebra, femur, or other bone may be identified in the image. In other embodiments, machine learning, artificial intelligence, and/or a neural network may be used to identify the at least one anatomical element. In such embodiments, a plurality of training images (each depicting on or more anatomical elements) may be provided to a processor such as the processor 104, and each training image may be annotated to include identifying information about an anatomical element in the image. The processor, executing instructions stored in memory such as the memory 116 or in another memory, may analyze the images using a machine-learning algorithm and, based on the analysis, generate one or more image processing algorithms for identifying anatomical elements in an image. Such image processing algorithms may then be applied to the at least one image.

The method 200 also comprises calculating an insertion point and a path for a rod (step 206). In some embodiments, the calculating can be performed automatically by an algorithm such as the algorithm 128. In other embodiments, the calculating can be performed by a surgeon or other user. The path is calculated from the insertion point to the at least one tower to position the rod in the at least one tower. The path may be calculated based on the identified soft tissue portion and the identified at least one anatomical element. For example, the path may be based on avoiding specific soft tissue features or anatomical elements.

Calculating the insertion point and/or the path may be based on one or more inputs. The inputs may include, for example, a geometry of the rod, a location of one or more towers through which the rod is to be inserted, and/or a target pose of the vertebrae to which the rod will be attached (e.g., via pedicle screws). The inputs may also include inputs needed to accomplish one or more objectives in connection with calculating the insertion point and/or the path. Such objectives may include, for example, avoiding main blood vessels, avoiding identified nerves and nerve roots, aligning the rod to run as parallel as possible to muscle structures, minimizing ligament transfers, minimizing needed rod rotations in a path of motion, avoiding rod insertion into or through organs, and/or avoiding rod collision with bony anatomy. The one or more inputs may be received via the user interface and/or the communication interface and may be stored in the memory. In some embodiments, the one or more inputs may be provided in or via a surgical plan. The one or more inputs may also be determined from the at least one image obtained in step 202 and processed in step 204.

The step 206 may include generating instructions for orienting the rod at the insertion point and moving the rod along the path. The instructions may be in machine readable form (such as the instructions 124) and/or human readable form. The instructions may be communicated to a surgeon or user via a user interface such as the user interface 112 and/or via a communication interface such as the communication interface 108. The instructions may also be communicated to a robot such as the robot 136 to cause a robotic arm such as the robotic arm 148 to execute the instructions.

The method 200 also comprises inserting the rod at the insertion point and along the path (step 208). In some embodiments, inserting the rod may be performed by a surgeon. In at least some of these embodiments, the instructions generated in step 206 may be communicated to the surgeon or a user for inserting the rod and moving it along the path. In other embodiments, a surgeon may be robotically assisted. For example, a robot may hold the rod, but the robot may move based on input from the surgeon.

In other embodiments, a robotic arm such as the robotic arm 148 may insert the rod. The robotic arm may hold or otherwise support the rod to orient the rod and/or move the rod. The instructions generated in step 206 may be transmitted to the robot to cause the robotic arm to orient the rod at the insertion point and to move the rod along the path.

The method 200 also comprises tracking the rod (step 210). Tracking the rod may comprise using a navigation system such as the navigation system 156, a tracking marker such as the tracking marker 152, and/or a sensor such as the sensor 144 to enable determination of a pose (e.g., a position and orientation) of the rod at any given time. For example, a marker may be attached to the rod (e.g., to a proximal end of the rod, so as to be visible while the distal end of the rod is inserted into the patient) and the marker may be tracked by a navigation camera. In another example the rod may be supported and manipulated by an accurate robotic arm (e.g., a robotic arm whose pose relative to at least a robotic coordinate system is always known) such as the robotic arm 148, and information about a pose of the robotic arm, and thus of the rod, may be obtained from the robot. In yet another example, a sensor may be disposed on or integrated with the rod and/or the robotic arm and the sensor may transmit or otherwise provide information about a position of the rod. The sensor may be, for example, an inertial measurement unit.

The step 210 may also include tracking at least a soft tissue portion surrounding the rod. The soft tissue portion may be tracked or otherwise monitored in real-time by an imaging device such as the imaging device 132. The soft tissue portion may be tracked to monitor for damage to the soft tissue or to prevent damage to the soft tissue. A position of the soft tissue portion may also be tracked or otherwise monitored, whether to ensure that the calculated path remains available or for any other purpose. The soft tissue portion may be tracked, for example, using an imaging device capable of detecting soft tissue, or in any other manner. An alert or notification may be generated and communicated to the surgeon or user to indicate when undesired damage has occurred or may occur to the soft tissue. The alert or notification may be communicated via a user interface such as the user interface 112.

The method 200 also comprises determining a difference between a position and/or an orientation of the rod and the path (step 212). The position and/or the orientation of the rod may be obtained from step 210 described above. In some embodiments, the determining can be performed automatically by an algorithm such as the algorithm 128. In other embodiments, the determining can be performed by a surgeon or other user. The position and orientation, or pose, of the rod may be determined in a robotic coordinate system or another coordinate system in which the path was originally determined or into which the path has been translated, so that the pose of the rod and the path can be compared in a single coordinate system.

In some embodiments, the difference may be determined continuously during insertion of the rod. In other embodiments, the difference may be determined at predetermined increments. The predetermined increments may be based on time (e.g., every 5 seconds), distance (e.g., every quarter inch), and/or percentage of completion of the path (e.g., every 5% of completion of the path). The difference may be displayed or otherwise communicated to a surgeon or user.

The actual pose of the rod may vary from the path for various reasons. In some embodiments, a pose of the patient may cause soft tissue of the patient's anatomy to shift in a way that obstructs the originally calculated path, exerts an unexpected force on the rod during insertion thereof, or otherwise renders the originally calculated path unworkable. In some instances, the rod may be defective and bend or otherwise deform unexpectedly. In still other situations, a previously undetected obstacle may be identified during insertion of the rod, and may necessitate altering the calculated path. In still other embodiments, one or more pedicle screws to which the rod is being attached may dislodge from the vertebra in which it is implanted, or the vertebra may break, or placement of the rod in a pedicle screw attached to one vertebra may cause a vertebra to which another pedicle screw is attached to move out of the calculated path. Any one or more of these reasons, and/or any other reason, may result in the rod having a pose that varies from the path.

The method 200 also comprises updating the path (step 214). In some embodiments, the path may be updated based on detected movement of the soft tissue portion. The movement may be detected when the difference determined, for example, in step 212 meets a threshold. In other embodiments where at least one tower may be tracked (as described with respect to method 300 below), the path may be updated based on detected movement of at least one tower. In some embodiments, the updating can be performed automatically by an algorithm such as the algorithm 128. In other embodiments, the updating can be performed by a surgeon or other user. Updating the path may include updating the insertion point (e.g., calculating a new insertion point), the entire path, or a portion of the path. For example, the path may be updated from a current position of the rod (in other words, a remaining portion of the path may be updated). In another example, the rod may be removed and the entire path and/or the insertion point may be updated. Updating the path may also include adjusting an orientation of the rod and/or a position of the rod at one or more points in the path. The updated path may be provided to a robot that is being used to insert the rod, or the updated path may be communicated to a surgeon or user and may be communicated via a user interface such as the user interface 112. In some embodiments, a new rod direction and/or rod orientation may be displayed or communicated to the surgeon.

The step 214 may also include updating one or more steps of the surgical plan. The updated path may require one or more steps to be removed, added, or adjusted based on the new path. For example, the updated path may require a new order for tightening set screws of corresponding pedicle screws.

The step 214 may also include generating updated instructions based on the updated path. In some embodiments, the updated instructions may be human readable and communicated to a surgeon. In other embodiments, the updated instructions may be machine readable and communicated to the robot to cause the robotic arm to move the rod along the new path. The updated instructions may also cause the robotic arm to remove the rod from the current path and reorient the rod to move the rod along the updated path.

The step 214 may also include triggering an alert or an alarm to notify the surgeon that the threshold has been met by the difference. The alert or alarm may also notify the surgeon that the path has been updated and may prompt the surgeon to accept the updated path. In some embodiments, the threshold may be received via the user interface and/or the communication interface and may be stored in the memory. In other embodiments, the threshold may be provided in or via a surgical plan. In at least one embodiment, the threshold may be 1mm. In other embodiments, the threshold may be less than or greater than 1mm. In some embodiments, the difference may be calculated based on a maximum displacement of any point on the rod from a corresponding point on the path. In other embodiments, the difference may be calculated based on a displacement of a tip of the rod from the path. In still other embodiments, the difference may be calculated as an angle of rotation between the actual orientation of the rod and an orientation that matches the path. Thus, for example, if a rod is fully inserted in an orientation that results in the least resistance, and then must be rotated into a final position, the difference may be the angle by which the rod needs to be rotated to reach the final position.

Turning now to FIG. 3, a method 300 of inserting a rod may be carried out or otherwise performed, for example, by at least one processor. The at least one processor may be the same as or similar to the processor(s) 104 of the computing device 102 described above. The at least one processor may be part of a robot (such as a robot 136) or part of a navigation system (such as a navigation system 156). A processor other than any processor described herein may also be used to execute the method 300. The at least one processor may perform the method 300 by executing instructions stored in a memory, such as the instructions 124 of the memory 116. The instructions may correspond to one or more steps of the method 300 described below. The instructions may cause the processor to execute one or more algorithms, such as the algorithms 128. For example, one or more such algorithms 128 may be used to map one coordinate system to another coordinate system once each coordinate system has been located, and/or to calculate an insertion point and a path, and/or to generate rod insertion instructions.

The method 300 comprises receiving information about a current position of at least one tower (step 302). In some embodiments, the information is sensor data obtained from a sensor such as the sensor 144. In some embodiments, the sensor is disposed on or integrated with the at least one tower. In other embodiments, the sensor may be disposed on or integrated with a robotic arm such as the robotic arm 148. The sensor may be, for example, an inertial measurement unit.

In some embodiments, a first robotic arm may support and move the rod and a second robotic arm may support the at least one tower at a known position and/or orientation. The first robotic arm and/or the second robotic arm may be the same as or similar to the robotic arm 148. In such embodiments, information about a current position and/or orientation of the second robotic arm, and thus the at least one tower, may be obtained (e.g., from one or more sensors 144 disposed on the second robotic arm).

In yet another example, a sensor may be disposed on or integrated with the at least one tower and a redundant sensor may be disposed on or integrated with the second robotic arm, and each sensor may be tracked or may transmit information about a current position of the at least one tower.

In still other embodiments, the information may be received from a navigation system such as the navigation system 156. In such embodiments, the at least one tower and/or the first robotic arm may comprise a tracking marker such as the tracking marker 152 (which may, in some embodiments, be a navigation LED) and/or another device detectable by the navigation system 156, which the navigation system 156 may use to determine a pose of the at least one tower. The tracking marker may be positioned on or integrated with the at least one tower and/or the first robotic arm. In these and other embodiments, the information may comprise image data obtained via a camera or other imaging sensor.

The method 300 also comprises tracking the at least one tower to identify a tower movement (step 304). Tracking the at least one tower may use a navigation system such as the navigation system 156, a tracking marker such as the tracking marker 152, and/or a sensor such as the sensor 144. For example, a marker may be attached to the at least one tower and the marker may be tracked by a navigation camera. The marker may also be attached or secured to a robotic arm such as the robotic arm 148 holding the at least one tower and the marker may be tracked by the navigation camera.

Tracking the at least one tower may include comparing a current position and/or orientation of the at least one tower and an expected or known position and/or orientation of the at least one tower to identify the tower movement. The current position and/or orientation of the at least one tower may be obtained in step 302. The current position and/or the orientation of the at least one tower may then be compared to the known position and/or orientation (e.g., as determined from previously obtained sensor data or otherwise) to determine if a difference exists. If a difference exists between the current and the known position and/or orientation exists, then this difference indicates that the at least one tower has moved. The difference may then be quantified to determine a magnitude of the movement.

Identified tower movement may indicate that insertion of the rod is offset from a calculated path (described below with respect to step 306) or otherwise is no longer on the calculated path. Identified tower movement may also indicate that the calculated path is no longer a feasible path for inserting the rod into the tower (because the tower no longer lies along the calculated path). In some embodiments, identified tower movement may trigger one or more additional actions, such as recalculating a path, or causing the robotic arm to move the tower back to a position on a previously calculated path.

The method 300 also comprises calculating an insertion point and a path (step 306). The step 306 is the same as or similar to the step 206 of the method 200 described above.

Further, calculating the insertion point and the path may be based on the current position and/or orientation of the at least one tower identified in step 302. For example, the current position and/or orientation of the at least one tower may be different than an expected or known position and/or orientation of the tower (as reflected, for example, in preoperative imagery, a surgical plan, or even the sensor data received in the step 302). Rather than moving the at least one tower to the known position and/or orientation (e.g., using a robotic arm), the insertion point and the path may be calculated or recalculated based on the current position and/or orientation.

The method 300 also comprises causing a robotic arm to insert a rod at the insertion point and along the path (step 308). The step 308 is the same as or similar to the step 208 of the method 200 described above with respect to insertion of the rod by a robotic arm.

The method 300 also comprises causing the robotic arm to adjust the path during insertion of the rod based on the tower movement (step 310). In some embodiments, the adjusting may be based on the use of an algorithm such as the algorithm 128 executed by a processor such as the processor 104 or a processor of the robotic arm. The adjusting may be performed automatically. Adjusting the path may include adjusting the insertion point (e.g., calculating a new insertion point), the entire path, or a portion of the path. For example, the path may be adjusted from a current position of the rod (in other words, a remaining portion of the path may be adjusted). In another example, the rod may be removed and the entire path and/or the insertion point may be adjusted. Adjusting the path may also include adjusting an orientation of the rod and/or a position of the rod at a number of points in the path.

In some embodiments, such as where each of the at least one towers has moved an equal increment, the remaining portion or the entire path may be shifted by the increment. For example, if each tower of a plurality of towers have moved 1 cm in a particular direction, then the path may be shifted 1 cm in the same direction.

The step 310 may also include generating and transmitting updated instructions based on the adjusted path to the robotic arm to cause the robotic arm to move the rod along the adjusted path. The updated instructions may also cause the robotic arm to remove the rod from the current path and re-orient the rod to move the rod along the adjusted path.

The step 310 may also include triggering an alert or an alarm to notify the surgeon that tower movement has been identified. The alert or alarm may also notify the surgeon that the path has been adjusted and may prompt the surgeon to accept the adjusted path prior to the robotic arm moving the rod along the adjusted path. In some embodiments, a surgeon or other user may provide input to modify the adjusted path.

In embodiments where a first robotic arm moves the rod and a second robotic arm supports the at least one tower, the method 300 also comprises causing the second robotic arm to adjust a position and/or an orientation of the at least one tower (step 312). In some embodiments, the position and/or orientation of the at least one tower may be adjusted to move the at least one tower back to the known position and/or orientation. In other embodiments, the at least one tower may be adjusted to accommodate the rod path. In further embodiments, where tower movement is identified and a current position and/or orientation of the rod does not match the path, the at least one tower may be adjusted to accommodate the current position and/or orientation of the rod.

In some embodiments, the step 312 may occur only to the extent that a force exerted by the second robotic arm on the at least one tower does not exceed a predetermined threshold. The threshold may be an absolute magnitude or a relative magnitude. The predetermined threshold may be generated automatically based on information about, for example, a pedicle screw to which the tower is connected (e.g., a length of the pedicle screw, a width of the pedicle screw) and/or information about the vertebra to which the tower is attached via a pedicle screw (e.g., dimensions of the vertebra, bone quality of the vertebra). Alternatively, the predetermined threshold may be input by a surgeon or other user. In still further embodiments, a recommended predetermined threshold may be generated automatically, and a surgeon or other user may modify and/or approve the recommended predetermined threshold. The force exerted by the second robotic arm on the at least one tower may be measured, for example, by one or more sensors (e.g., sensors 144) on the second robotic arm.

It will be appreciated that steps 310 and 312 may occur within sequence or simultaneously. For example, when tower movement is identified, the path of the rod and the position of the at least one tower may both be adjusted. In another example, the path of the rod may be adjusted, then the position of the at least one tower may be adjusted, or vice versa. Further, the steps 310 and 312 may optimize a placement of the rod in the at least one tower based on the current positions and/or orientations of the at least one tower and/or rod. In some embodiments, the pose of the at least one tower may be adjusted until the predetermined threshold is reached, and the path may then be calculated based on the resulting position of the at least one tower.

The method 300 also comprises monitoring a magnitude of a force received by the robotic arm (step 314). The robotic arm that receives the force may be the robotic arm attached to the at least one tower (as described above in connection with the step 312), or alternatively may be the robotic arm manipulating the rod. The force may be detected with a sensor such as a sensor 144. The detected force may be or comprise a linear force, rotational force (e.g., torque), and/or any other type of force. The sensor may be positioned on the robotic arm or elsewhere. The sensor may be configured to detect motion of the robotic arm and to calculate a force based on information about a stiffness of the robotic arm as well as the detected motion. Alternatively, the sensor may be configured to measure force directly. Any type of sensor capable of direct measurement of force, or of calculation of force based on some other measurement, may be used to detect the force for purposes of the step 314. In some embodiments, the detected force may comprise one or more individual force components (e.g., a force component in each of an X-axis, a Y-axis, and a Z-axis, and/or a torque component around an X-axis, a Y-axis, and a Z-axis).

The method 300 also comprises causing the robotic arm manipulating the rod to pause movement of the rod when the magnitude of the force meets a predetermined threshold (step 316). The predetermined threshold may be determined in any manner described herein or in any other manner. The step 316 may include generating, transmitting, and/or executing instructions such as the instructions 124 when the magnitude of the force meets the predetermined threshold to cause the robotic arm to pause movement. The instructions may further cause the robotic arm to remove the rod from the path and/or the insertion point when the magnitude of the force meets the predetermined threshold.

The step 316 may comprise comparing the detected force to the predetermined threshold. The comparing may comprise comparing a single combined force vector to a predetermined threshold, and/or comparing individual force components to individual force thresholds. The detected force may be considered to be lower than the predetermined threshold if the overall force vector has a lower magnitude than the predetermined threshold, or the detected force may be considered to be lower than the predetermined threshold if any individual force component exceeds a corresponding predetermined threshold component (and/or regardless of whether the overall force vector has a lower magnitude than the predetermined threshold).

Additionally, in some embodiments, the predetermined threshold may comprise a threshold magnitude that depends on a direction of the detected force vector. Thus, for example, the predetermined threshold may comprise a first threshold magnitude for a force exerted in a first direction, and a second threshold magnitude different than the first threshold magnitude for a force exerted in a second direction different than the first direction. As referenced above, the predetermined threshold may comprise individual components (e.g., in the X-axis, Y-axis, and Z-axis directions, and/or around the X-axis, the Y-axis, and the Z-axis) or may simply comprise an overall threshold magnitude and direction. In still other embodiments, the predetermined threshold may comprise only a threshold magnitude.

The method 300 also comprises verifying placement of the rod in the at least one tower (step 318). Placement of the rod may be verified using a laser pointer and reflector disposed on or integrated with the rod, a navigation system such as the navigation system 156, a tracking marker such as the tracking marker 152, and/or a sensor such as the sensor 144.

In embodiments where a first robotic arm moves the rod and a second robotic arm supports the at least one tower, placement of the rod may be verified by the second robotic arm. A sensor disposed on or integrated with the second robotic arm may sense the rod placed in the at least tower. For example, an accelerometer may be configured to sense vibrations and/or other movement of the at least one tower (and/or an associated pedicle screw) caused by movement of the rod through the tower.

In other embodiments, an electrical circuit may be utilized to verify placement of the rod in the at least one tower. The circuit may be between a first robotic arm supporting the rod and a second robotic arm supporting the at least one tower. More specifically, where the rod and the tower are both metallic or otherwise conductive, an electrical signal may be transmitted through the rod, and a sensor on the second robotic arm may be used to detect whether the signal is transmitted through the at least one tower (which would suggest that the rod and the at least one tower are in contact). The reverse could also be done (e.g., the electrical signal could be introduced to the tower, and detected at the rod). Alternatively, an electrical signal could be introduced on a first side of the tower and detected on an opposite second side of the tower that is insulated from the first side of the tower. If the signal is detected, then an inference could be made that the rod has been properly placed between the two sides of the tower and has placed the two sides in electrical communication with each other. An electrical circuit created as described above or in any other manner may thus be used to determine whether the rod has been properly placed within each of the at least one tower.

The method 300 also comprises causing the robotic arm to tighten a set screw (step 320). The robotic arm may be the same robotic arm that is (or was) attached to the at least one tower, and may support a tool, such as a screwdriver, to tighten the set screw in the tower and/or the head of the pedicle screw. In embodiments where a plurality of set screws is tightened for a plurality of corresponding pedicle screws, each set screw may be incrementally tightened in a sequence to avoid point loading any single pedicle screw. For example, a first set screw may be tightened, then a second set screw may be tightened, then the first set screw may be further tightened, etc.

In some embodiments, the robotic arm that inserted the rod may also tighten the set screw. In other embodiments, a different robotic arm may tighten the set screw.

The method 300 also comprises causing the robotic arm to remove the at least one tower from a head of a pedicle screw (step 322). The robotic arm may support and operate a tool to grasp the at least one tower and apply a force to detach, disconnect, break, or otherwise remove the least one tower from the head. The robotic arm may also apply a force to the at least one tower to break the at least one tower using any sort of tool or by simply pressing an end of the robotic arm against the tower.

The at least one tower may include a score to facilitate breakage of the at least one tower from the head. In some embodiments, the robotic arm that inserted the rod may also remove the at least one tower. In other embodiments, a different robotic arm may remove the at least one tower.

As may be appreciated based on the foregoing disclosure, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). One or more steps of the methods described herein may be performed in an order other than the order in which they are described herein.

For the avoidance of doubt, aspects of the present disclosure may be utilized to automatically or with robotic assistance calculate a path for insertion of a rod through one, two, three, four, five, six, seven, eight, nine, ten, or more towers extending from implanted pedicle screws. The methods described herein may be carried out using two robotic arms (with one robotic arm manipulating the rod and a second holding or manipulating one of the towers at a time), or using more than two robotic arms (with each additional robotic arm configured to hold or manipulate another one of the towers). As may be appreciated, the greater the number of robotic arms, the greater the number of towers that may be held or manipulated simultaneously. As a result, where a rod is to be inserted through a plurality of pedicle screw towers, and a plurality of robotic arms are available to hold and/or manipulate each of the plurality of pedicle screw towers, the plurality of robotic arms may be caused to align (or to otherwise arrange) the plurality of pedicle screw towers to facilitate insertion of the rod therein. Of course, any such manipulation of the pedicle screw towers may be limited by an amount of force that may be safely applied to each pedicle screw tower by a corresponding robotic arm, and so perfect alignment or other arrangement of the pedicle screw towers (e.g., according to a surgical plan) may not be possible.

Also in some embodiments, a single robotic arm may be provided with an end effector (or otherwise equipped to be) capable of connecting to, and/or of manipulating, multiple pedicle screw towers simultaneously. In such embodiments, a plurality of pedicle screw towers may be held or otherwise manipulated using a single robotic arm, while another robotic arm manipulates a rod.

In still further embodiments of the present disclosure, only a single robotic arm may be available, which robotic arm may be used either to insert the rod or to hold and/or manipulate one or more pedicle screw towers. Whichever task(s) is/are not accomplished by the robotic arm may be carried out by a surgeon or other user, whether based on instructions displayed on a user interface or otherwise.

Embodiments of the present disclosure beneficially provide for rod insertion planning and rod insertion that accounts for tower movement. By adjusting a path of the rod and/or position of a tower, placement of the rod in the tower may be optimized in real-time during the procedure, thereby preventing placement of the rod that may cause unforeseen issues due to inaccurate placement. Further, planning of the rod insertion and path may be optimized to reduce trauma to soft tissue or other anatomical elements in the path. Thus, patient safety may be increased and soft tissue and/or anatomical element trauma may be reduced.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for calculating an insertion point and a path for a rod, comprising:
  receiving a surgical plan having at least one image and information about a position of at least one tower, the at least one image depicting a surgical region for a robotic or robot-assisted minimally invasive surgery (MIS) procedure;
  identifying, in the at least one image, a soft tissue portion and at least one anatomical element;
  calculating an insertion point and a path from the insertion point to the at least one tower for a rod based on the identified soft tissue portion and at least one anatomical element;
  generating, based on the calculating, machine readable instructions for use by a robotic arm to move for orienting the rod at the insertion point and moving the rod along the path;
  commencing the MIS procedure by causing the robotic arm to move according to the machine readable instructions to thereby:
    insert the rod at the calculated insertion point; and
    begin moving the rod along the calculated path;
  tracking at least the rod and the identified soft tissue portion following the commencement of the MIS procedure and in a coordinate system usable by the robotic arm;
  determining, based on the tracking and on a periodic or continuous basis, whether a difference between a current pose of the robotic arm and an expected pose of the robotic arm along the calculated path meets a threshold;
  updating the path for the rod in response to determining that the difference meets the threshold; and
  generating, based on the updating, updated machine readable instructions for use by the robotic arm to move for implementing a corrective action.

2. The method of claim 1, wherein the at least one image is obtained from at least one of an MRI scanner, an ultrasound, or a CT scanner.

3. The method of claim 1, wherein the at least one image comprises a first image and a second image of the surgical region, the first image comprising hard tissue information and the second image comprising soft tissue information.

4. The method of claim 3, wherein the first image is generated using a first imaging modality and the second image is generated using a second imaging modality.

5. The method of claim 1, further comprising:
  further in response to determining that the difference meets the threshold, creating and transmitting an alert to initiate a human review of the pose of the robotic arm comprising obtaining one or more additional images of the surgical region; and upon completion of the human review, causing the robotic arm to move according to the updated machine readable instructions to thereby implement the corrective action.

6. The method of claim 3, wherein one of the first and second images is a preoperative image, and another of the first and second images is an intraoperative image.

7. The method of claim 1, wherein calculating the insertion point and the path is based on one or more inputs.

8. The method of claim 1, wherein identifying the at least one anatomical element uses at least one of feature recognition, machine learning, artificial intelligence, or a neural network.

9. The method of claim 1, wherein identifying the soft tissue portion uses segmentation.

10. The method of claim 1, wherein calculating the insertion point and the path is based on information about a geometry of the rod.

11. The method of claim 1, further comprising detecting, based on the tracking, movement of the soft tissue portion following the commencement of the MIS procedure, wherein updating the path for the rod comprises updating the path for the rod in response to detecting the movement of the soft tissue portion and based on characteristics of the movement of the soft tissue pertaining to the currently calculated path or an updated path for the rod.

12. The method of claim 1, wherein the tracking comprises tracking the at least one tower, wherein the method further comprises detecting, based on the tracking, movement of the at least one tower following the commencement of the MIS procedure, and wherein updating the path for the rod comprises updating the path for the rod in response to detecting the movement of the at least one tower based on characteristics of the movement of the at least one tower.

13. A method for inserting a rod, comprising:
  receiving a surgical plan having information about an insertion point and a path of a rod to at least one tower, wherein the information includes at least one image depicting a surgical region for a robotic or robot-assisted minimally invasive surgery (MIS) procedure;
  identifying, in the at least one image, a soft tissue portion and at least one anatomical element;
  generating machine readable instructions for use by a robotic arm to move for orienting the rod at the insertion point and moving the rod along the path;
  commencing the MIS procedure by causing the robotic arm to move according to the machine readable instructions to thereby:
    insert the rod at the insertion point; and
    begin moving the rod along the path;
  tracking at least the rod during insertion of the rod using the path following the commencement of the MIS procedure and in a coordinate system usable by the robotic arm;
  determining, based on the tracking, a difference between a pose of the rod and the path;
  updating the path when the difference meets a threshold; and
  implementing a corrective action using the robotic arm according to the updated path.

14. The method of claim 13, further comprising communicating the updated path to a user.

15. The method of claim 13, wherein the tracking comprises tracking a soft tissue portion surrounding the rod.

16. The method of claim 13, further comprising:

calculating the insertion point and path from the insertion point to the at least one tower based on the identified soft tissue portion and at least one anatomical element.

17. The method of claim 13, wherein the tracking comprises tracking at least the rod using at least one of a navigation system, a marker, or a sensor.

18. A system for calculating an insertion point and a path for a rod, comprising:

at least one processor; and at least one memory storing instructions for execution by the at least one processor that, when executed, cause the at least one processor to:

receive a surgical plan having at least one image and information about a position of at least one tower, the at least one image depicting a surgical region for a robotic or robot-assisted minimally invasive surgery (MIS) procedure;

identify, in the at least one image, a soft tissue portion and at least one anatomical element;

calculate an insertion point and path from the insertion point to the at least one tower for a rod based on the identified soft tissue portion and at least one anatomical element, the at least one tower extending from an implanted pedicle screw;

generate, based on the calculated insertion point and path, machine readable instructions for use by a robot to orient the rod at the insertion point and move the rod along the path;

cause the robot to execute the machine readable instructions to thereby:

insert the rod at the calculated insertion point; and move the rod along the calculated path;

track at least the rod following the insertion of the rod by the robot and in a coordinate system usable by the robot;

determine, based on the tracking of the rod and on a continuous or periodic basis, whether a difference between a current pose of the rod and an expected pose of the rod along the calculated path meets a threshold; and in response to the difference being determined to meet the threshold:

receive an updated image of the surgical region including at least a portion of the rod;

compute an updated path for the rod based at least in part on the updated image; and generate, based on the updated path, updated machine readable instructions for execution by the robot to implement a corrective action according to the updated path.

19. The system of claim 18, wherein the at least one image is obtained from at least one of an MRI scanner, an ultrasound, or a CT scanner.

20. The system of claim 18, wherein the at least one image comprises a first image and a second image of the surgical region, the first image comprising hard tissue information and the second image comprising soft tissue information.

* * * * *